United States Patent [19]

Mast et al.

[11] Patent Number: 4,865,456
[45] Date of Patent: Sep. 12, 1989

[54] MEASURING HEAD

[75] Inventors: Fred Mast, Wil; Jean A. Knus, Zurich, both of Switzerland

[73] Assignee: Gretag Aktiengesellschaft, Regensdorf, Switzerland

[21] Appl. No.: 238,586

[22] Filed: Aug. 31, 1988

[30] Foreign Application Priority Data

Oct. 1, 1987 [CH] Switzerland .................. 3821/87

[51] Int. Cl.[4] ................ G01N 21/47; G02B 21/04
[52] U.S. Cl. .................................. 356/446; 350/444
[58] Field of Search ............... 356/445, 446, 447, 448; 350/444

[56] References Cited

U.S. PATENT DOCUMENTS

| 3,244,062 | 4/1966 | Sweet | 356/445 |
| 3,825,322 | 7/1974 | Mast | 350/444 |
| 4,076,421 | 2/1978 | Kishner | 356/446 |
| 4,078,858 | 3/1978 | Mast | 356/446 |

FOREIGN PATENT DOCUMENTS 209860 1/1987 European Pat. Off. .
3421577 12/1985 Fed. Rep. of Germany .

OTHER PUBLICATIONS

"The Mangin Mirror as Imaging Element" (Riedl) 2450 Electro Optics, (1983) Jun., No. 6, Chicago, Ill., pp. 50–54.
European Search Report No. RS 79804 CH.

Primary Examiner—Vincent P. McGraw
Attorney, Agent, or Firm—Burns, Doane, Swecker & Mathis

[57] ABSTRACT

A measuring head for the determination of the optical reflectance properties of color measuring fields co-printed with color sheets includes an optical illuminating device having two Mangin mirrors and an aplanar system located in alignment with the Mangin mirrors in a central opening. The light emitted by a light source and reflected by the measuring area arrives in a glass rod and is fed through an optical measuring device into a light waveguide, through which the reflected light is fed into a spectrometer for spectral analysis.

12 Claims, 1 Drawing Sheet

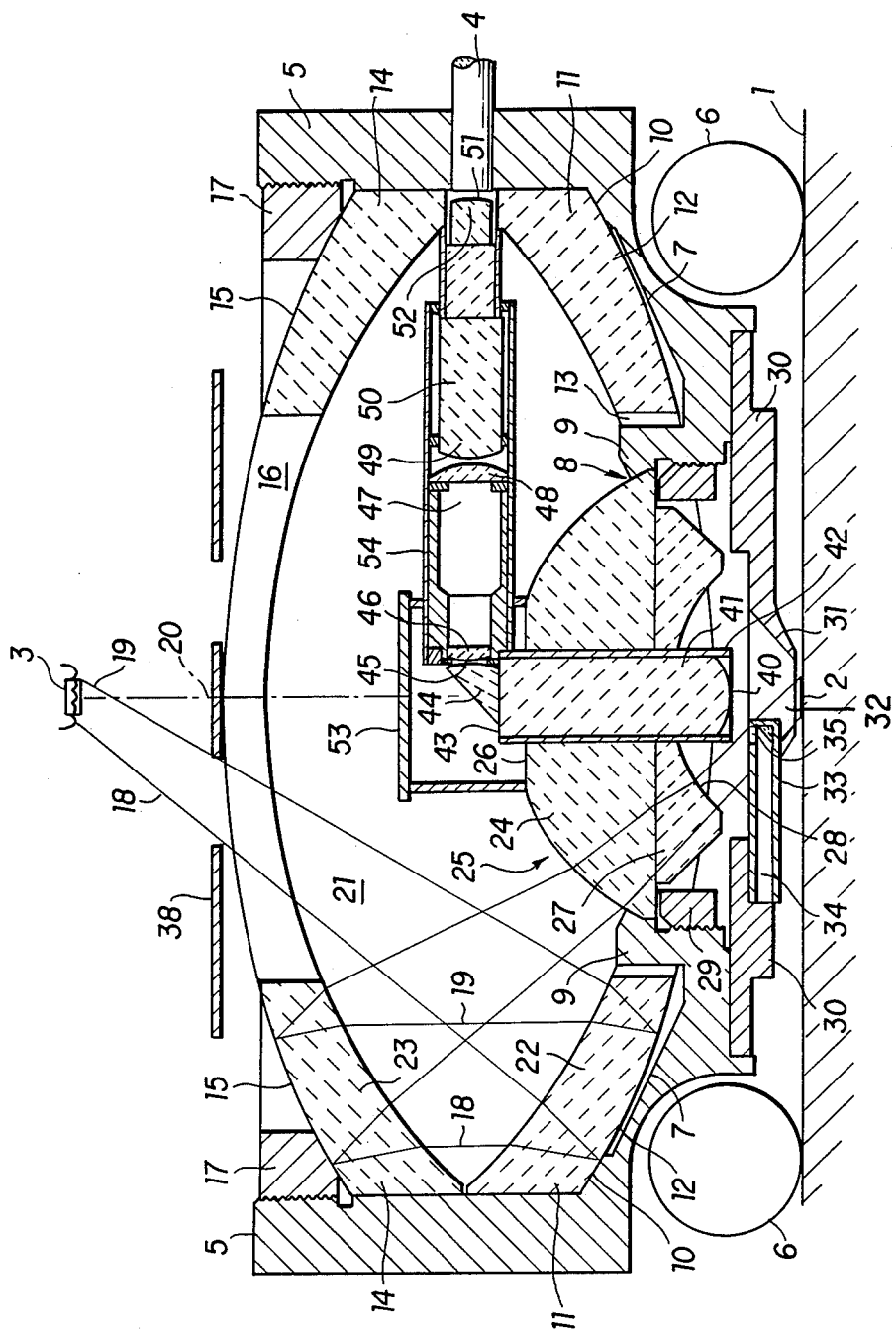

MEASURING HEAD

BACKGROUND OF THE INVENTION

The invention relates to a measuring head for a photoelectric measuring device, in particular a spectral reflectance measuring instrument, which includes, a source of light and an optical illuminating means which illuminates a measuring area located at a predetermined distance from the measuring head on a measuring plane at a given large angle of incidence. The device also includes an optical measuring means, the objective lens of which captures the measuring light reflected by a measuring surface in a small measuring angle range with respect to the perpendicular of the measuring surface and is connected by means of a beam waveguide with a photoelectric transformer layout, in particular a spectrometer.

A measuring head for determining optical reflectance properties which includes optical projection means to illuminate the measuring surface and optical collector means comprising an annular mirror for receiving the light reflected from the measuring surface at a predetermined angle relative to the optical axis of the optical projection or illuminating means, is known from DE 26 00 604.

It is also state of the art to evaluate the color measuring fields provided on a printed sheet, in order to improve the inking controls of an offset printing machine, not merely densitometrically, but also colorimetrically by spectral measurements. In the process, spectral reflections are used for color matching and color coordinates are calculated from them. The color coordinates are compared with corresponding set color coordinates to form resulting color deviation signals for the regulation of inking controls. To avoid measuring errors and thus errors in the control of the inking process, it is necessary to determine the color location for the co-printed color measuring fields with a high degree of accuracy over the entire wave length range. While in the case of densitometers illumination variations of the order of 2.5% due to distance variations between the illuminating means and the measuring surface may still be tolerable, such measuring errors in spectral analysis lead to undesirable errors in measuring. According to EP-A-209 860, attempts are being made to eliminate the problem by locating the source of light at the focal point of a condenser and by ensuring that the measuring area is smaller than the core area within the surface illuminated on the measuring plane. However, a relatively large amount of light is wasted in the process and the accuracy of this known apparatus is still capable of being improved.

SUMMARY OF THE INVENTION

It is an object of the present invention to provide a measuring head of the above-mentioned type, whereby it is possible to illuminate a measuring area under a large angle and to measure the light reflected at a small angle for all of the colors independently of variations in distance. Such variations are due, for example, to the non-level placement of the printed sheet on its support, and in actual practice can never be completely eliminated.

This object is attained according to the invention by having the source of light located on the optical axis of an arrangement of two annular Mangin mirrors aligned parallel to the measuring plane. The two Mangin mirrors face each other with their concavely shaped sides and reproduce in the measuring plane an image of the light source located at a distance from the mirrors through a coaxial aplanatic lens, which corrects the color errors of the Mangin mirrors. Additionally the inlet lens of an objective lens system is located on the optical axis of the Mangin mirrors, and a measuring diaphragm coupled to a light-waveguide is provided at the focal point of the inlet lens.

The optical illumination means make it possible to illuminate a measuring area at an angle of incidence of essentially $45° \pm 5°$ on all sides with light originating in the source of light, whereby the measuring light reflected from the measuring surface into the optical measuring means is received at a measuring angle of essentially $0° \pm 5°$. The Mangin mirror layout of the illuminating means together with the coaxial aplanatic lens makes it possible to reproduce the light source accurately onto the measuring plane. As the two Mangin mirrors are constructed and located symmetrically and are cooperating with an aplanatic lens, the spherical aberration and the coma are eliminated by satisfying the sinus condition. The color errors of the Mangin mirror layout are compensated by the aplanatic lens. In this manner, for all colours images of the light source of equal size are generated in the measuring plane, whereby measuring errors which might occur if images of the light source in the various spectral colors were present not only on the measuring plane, but also above and below it, are avoided.

Using the layout and alignment of the present invention, the optical measuring or collector means always detects the measuring light reflected at the same spatial angle, even in the case of unavoidable distance variations of the measuring surface as mentioned previously. Intensity fluctuations due to such distance variations are thereby largely avoided.

BRIEF DESCRIPTION OF THE DRAWINGS

Other objects and advantages of the present invention will become apparent from the following detailed description of a preferred embodiment as described in conjunction with the accompanying drawing in which:

The single FIGURE shows a cross-sectional view of a measuring head in accordance with a preferred embodiment of the present invention.

DETAILED DESCRIPTION OF THE PREFERRED EMBODIMENT

The measuring head shown in the FIGURE serves to optically scan in succession individual measuring areas 2 on a measuring plane 1 which were co-printed with the printed sheets as color measuring fields and whose color is to be detected with a high degree of accuracy for the colorimetric monitoring and control of a printing machine. The measuring head shown in the FIGURE reproduces a schematically represented light source 3 on the measuring area 2 at a somewhat smaller scale and feeds part of the reflected light into a light beam waveguide 4 connected with a spectrometer, whereby the spectral color analysis is carried out.

The measuring head comprises an annular holder 5 with an external diameter of approximately 80 mm. The holder 5 is equipped with a plurality of rollers 6, which maintain the distance to the measuring plane 1 constant. A spring, not shown, is fastened to the measuring head and holds down the printed sheet located on the measuring plane 1. The measurement of the co-printed color measuring fields must be exact enough, so that even in the case of distance variations of for example ±0.2 mm relative to the measuring head (due to uneven support of the printed sheet), the measured values are distorted by less than one per mil over the entire wave length range. This requirement follows from the desirability of providing a color location determination with an accuracy of 0.1 E, which corresponds to the limit of color resolution for a trained eye.

The reproduction of the light source 3 takes place in a manner described in more detail below and occurs in an extremely achromatic fashion in order to insure that the imaging of the white light source 3 occurs in the same plane for all spectral colors and not into several planes displaced parallel to one another for the various spectral colors.

The holder 5 is located in the same housing with the light source 3, with no reflecting mirror being provided, in order to avoid imaging errors. The light source 3 consists of a flat coil halogen lamp with a color temperature of 3000 degrees. The flat coil covers a rectangular surface with a length of 2.6 mm and a width of 1.3 mm. The power consumption of the flat coil halogen lamp amounts to 30 Watts in the preferred embodiment. The plane of the flat coil extends parallel to the measuring plane 1, as shown schematically in the FIGURE.

The annular holder 5 of the measuring head comprises a funnel shaped bottom 7 with an annular nose 9 surrounding a circular opening 8 and an annular shoulder 10 in the area of the largest diameter of the funnel shaped bottom 7.

The annular shoulder 10 serves to support an annular first Mangin mirror 11, the reflective surface 12 of which is located on the convex side of the Mangin mirror 11. As seen in the FIGURE, the annular Mangin mirror 11 comprises a circular central opening 13, into which the peripheral nose 9 of the annular holder 5 protrudes from below.

The first Mangin mirror 11, which faces upward with its concave side, is associated with a second Mangin mirror 14, the concave side of which faces downward, and the reflective surface 15 of which is mounted on its upward facing convex side. The second Mangin mirror 14, like the first Mangin mirror 11, includes a circular central opening 16. The circular openings 13 and 16 have an internal diameter of 39 mm and an external diameter of 69 mm. An internal thread is provided in the vicinity of the upper edge of the circular holder 5, into which a clamping ring 17 is screwed to fasten the Mangin mirrors 11, 14 in the holder 5. To elucidate the (rotationally symmetrical) light beam path, the marginal rays 18 and 19 of a beam of light originating in the light source 3 and defined by a diaphragm 38, which is aligned on the optical axis 20 of the Mangin mirror 11, 14 above the second Mangin mirror 14 are shown in the drawing. In view of their rotational symmetry, the marginal rays 18 and 19 depicted in the left of the FIGURE, correspond to the marginal rays which exist in the right of the FIGURE, but which are not shown for the sake of clarity.

The light beam of the light source 3 indicated by the marginal rays 18, 19 passes through the opening 16 in the Mangin mirror 14 into the hollow space 21 between the identically constructed Mangin mirrors 11, 14 and is refracted upon its entry into the glass body 22 of the first Mangin mirror 11. Following reflection from the mirror surface 12, the beam of light exits after a second refraction from the glass body 22 in a manner such that the refracted and reflected central beam, not shown, passes between the marginal rays 18, 19 parallel to the optical axis 20 of the measuring head. This may be obtained by adjusting the distance of the light source 3 from the plane of symmetry between the two Mangin mirrors 11, 14.

As seen in the drawing, the radius of curvature of the mirrored surfaces 12, 15 is larger (about 71 mm) than the radius of curvature of the concave inner sides (about 49 mm). Following reflection from the mirror surface 15, the light beam exiting from the glass body 23 of the Mangin mirror 14, in particular the marginal rays 18, 19, passes into the first lens body 24 of the aplanar lens system 25. The first lens body 24 of the aplanar lens system 25 has a cap-shaped form, with a convex spherical surface facing in the direction of the light source 3 being provided with a flattening 26.

The first lens body 24 of the aplanar lens system 25 is associated with a second lens body 27 having the outer configuration of a truncated cone with a concave spherical outlet surface 28 as shown in the FIGURE. The aplanar lens system 25 consists in the conventional manner of two different glasses, with the external radius of the first lens body, in one embodiment of the present invention, being approximately 17 mm and the internal radius of the second lens being approximately 12 mm. The aplanar lens is dimensioned and adjusted to the Mangin mirror layout, which itself is aplanar, such that it compensates the color errors of the latter and the entire assembly is achromatic over the entire wave length range of interest.

The aplanar lens system 25 consisting of the lens bodies 24, 27 is tightly clamped against the peripheral nose 9 from below by means of a threaded ring 29. After passing through the aplanar lens system 25, the light of the annular light beam defined by the marginal rays 18, 19 impacts the measuring plane 1 at an angle of incidence of 45°±5°. In the FIGURE only the left cross-section through the annular beam of light is shown, but corresponding rays are present, which are incident from all sides and impact the measuring area 2 of the measuring plane 1. The measuring area 2, similar to the light source 3 which is shown at a slightly smaller scale, has a rectangular shape with the measuring area 2 forming a chromatically corrected light spot or measuring spot.

As seen in the FIGURE, the opening 8 of the holder 5 is provided with a cover 30 comprising a funnel shaped light-dispersion diaphragm 31 in its center. The opening 32 of the light-dispersion diaphragm 31 has an internal diameter of, for example, 54 mm and terminates with its lower edge approximately 0.5 mm above the measuring plane 1.

It is further seen in the FIGURE that a guide channel 33 is provided in the cover 30 for a reference beam waveguide or conductor 34, which makes it possible to capture the light incident on a reference surface 35 to form a reference intensity, which in the case of power fluctuations of the light source 3, permits the correction of measured values due to varying illumination intensities. The reference beam waveguide 34 protrudes radially from the outside into the area of the marginal rays 18, 19 and is bevelled at its front end, so that the light incident from above is diverted into the longitudinal direction of the conductor 34.

The layout described above with the two symmetrical Mangin mirrors 11, 14 and the aplanar system 25 makes it possible to produce a chromatically corrected image of the light source 3 on the measuring plane 1, so that in the case of distance variations due to the uneven support of the printed sheet, no chromatic displacement of the light scattered from the measuring surface takes place, as would be the case if the image of the light source 3 were to consist of several superposed images of different spectral colors.

The chromatically corrected illuminating means described is associated with the optical measuring means described below. Such a measuring means is insensitive to distance variations between the measuring head and the measuring plane. The measuring optics include an inlet lens 40 which is formed as the spherical surface of a glass rod 41. The glass rod 41 is located in a non-translucent sleeve 42 which extends along the optical axis of the measuring head through the aplanar, achromatic lens system 25. The glass rod 41 has a length of about 15 mm. Its inlet lens, with a radius of approximately 7 mm, is located at a distance approximately 5 mm above the measuring plane 1.

At its rear end 43, the glass rod 41 is connected with a deflecting prism 44, located in a deflection chamber 53 and through which the light reflected by the measuring spot is diverted into the plane of symmetry between the two Mangin mirrors in the FIGURE. As seen in the FIGURE, the right hand side of the deflecting prism 44 is shaped to a special plane against which a measuring diaphragm 45 is abutting. The measuring diaphragm 45 is located at the focal point of the inlet lens 40, so that the lens 40 converts the distance of the measuring diaphragm 45 into infinity. The system is thereby rendered insensitive to the aforementioned unavoidable distance variations. The measuring diaphragm 45 has an internal diameter of, for example, 2.2 mm. As seen in the FIGURE, a light protection tube 54 containing several optical components opens into the deflection chamber 53 located at the rear end of the aplanar system 25. The light protection tube 54 extends in the radial direction along the plane of symmetry between the two Mangin mirrors 11 and 14 up to their end.

To prevent the reception and measurement of dispersed light from outside the measuring area 2, the measuring area 2 is imaged by means of a lens 46 (and the surfaces 40 and 45), on a light-dispersion diaphragm 47 having an aperture with a diameter of approximately 4.5 mm. The diaphragm is located at a distance of about 11 mm from the lens 46.

In view of the fine grid structure of the measuring fields, optical fiber light wave conductors having a plurality of fibers may produce a moiree effect. To avoid this, a layout with two additional lenses 48, 49 forming a lens assembly is provided. The lens 48 is plano-convex as is the lens 46. The lens 49 is formed by a spherical surface which is shown as the left side of a transition glass rod 50 in the FIGURE. The transition glass rod 50 serves on the one hand to extend the path, and on the other, to adapt the diameter of the light waveguide 4. The transition glass rod 50 has a diameter which is reduced in two stages toward the direction of a frontal surface of the light waveguide 4. The lenses 48, 49 reproduce the image from the measuring diaphragm 45 on the frontal surface 51 which is shown in the FIGURE as being to the right of the transition glass rod 50. On the frontal surface 51, a lens 52 is provided which parallelizes the light diverted to the light waveguide 4. Although the opening angle of the light waveguide 4 may be, for example, ±11°, the light waveguide 4 is used with an opening of only 9° in order to provide greater assurance that any bending of the light waveguide 4 will not cause a change in the intensity of light. The length of the transition glass rod 50 is about 18 mm.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Measuring head for a photoelectric measuring device, comprising:
    a source of light;
    optical illumination means which illuminate a measuring area on a measuring plane located at a given distance from the measuring head, with a predetermined large angle of incidence, said illumination means including an arrangement of two annular Mangin mirrors with concave sides aligned parallel to the measuring plane and having an optical axis, said light source being located on said optical axis, and each of said mirrors having a concave side, the concave side of each of the two mirrors being placed so as to face one another;
    a coaxial aplanar system for reproducing said light source, which is located at a distance from the Mangin mirrors, so as to compensate for color errors of the Mangin mirrors on the measuring area;
    optical measuring means having a lens system which captures measuring light reflected from the measuring area within a small measuring angle range about a perpendicular of the measuring area and having a light waveguide means for connecting said lens system to a photoelectric transducer layout, said measuring means including an inlet lens which is included in the lens system and which is located on the optical axis of the Mangin mirrors; and, a measuring diaphragm which is located at the focal point of said inlet lens and which is connected to the light waveguide.

2. Measuring head according to claim 1, wherein said photoelectric measuring device is a spectral reflectance measuring instrument and wherein said photoelectric transducer layout is a spectrometer.

3. Measuring head according to claim 1, wherein the aplanar system extends into an intermediate space between the two Mangin mirrors and which further comprises a passage opening along its optical axis into which a glass rod optically disconnected relative to the aplanar system is protruding, said glass rod including said inlet lens at its front end facing the measuring area and said measuring diaphragm at its rear end.

4. Measuring head of claim 3, wherein said inlet lens includes a spherical light inlet surface.

5. Measuring head according to claim 3, wherein the measuring diaphragm is connected by a deflecting prism with the rear end of the glass rod.

6. Measuring head according to claim 3, wherein the measuring diaphragm is associated with a lens arrangement which images the measuring area on a light-dispersion diaphragm.

7. Measuring head according to claim 6, wherein a lens assembly is provided behind the light-dispersion diaphragm, said lens assembly imaging the measuring diaphragm on a frontal surface at an outlet of the measuring head toward the light waveguide.

8. Measuring head according to claim 7, wherein the lens assembly is located at a front end of a transition glass rod which faces the light-dispersion diaphragm, and the frontal surface is provided as a coupling surface at the rear end of the transition glass rod.

9. Measuring head according to claim 8, wherein a frontal surface of the light waveguide is connected with the frontal surface of the transition glass rod.

10. Measuring head according to claim 8, wherein the measuring diaphragm, the light-dispersion diaphragm and the transition glass rod with their associated lenses are located in a light protection tube extending to the ends of the Mangin mirrors in a radial direction along a plane of symmetry between the two Mangin mirrors.

11. Measuring head according to claim 10, wherein the light protection tube opens in the vicinity of the optical axis of the Mangin mirrors into a deflection chamber which is supported by a flattened rear side of the aplanar system and into which the glass rod is projecting with the deflecting prism.

12. Measuring head according to claim 1, wherein a reference light waveguide is provided, a front end of which protrudes into the light beam exiting from the aplanar system.

* * * * *